United States Patent [19]

Clifford et al.

[11] Patent Number: 5,433,749
[45] Date of Patent: Jul. 18, 1995

[54] APPARATUS FOR ENHANCING HEARING IN AN EAR

[76] Inventors: Jerome R. Clifford, 1941 Quail Run NE., Albuquerque, N. Mex. 87122; Karl L. Horn, 201 Cedar SE., Albuquerque, N. Mex. 87106

[21] Appl. No.: 27,362

[22] Filed: Mar. 8, 1993

[51] Int. Cl.⁶ .................................................. A61F 2/18
[52] U.S. Cl. ........................................ 623/10; 600/25
[58] Field of Search .................... 623/10; 606/61, 73, 606/60, 75; 181/130–135; 600/25

[56] References Cited

U.S. PATENT DOCUMENTS

| | | |
|---|---|---|
| 3,191,188 | 6/1965 | Mercandino et al. . |
| 3,196,462 | 7/1965 | Robinson . |
| 3,473,170 | 10/1969 | Haase et al. . |
| 3,710,399 | 1/1973 | Hurst . |
| 3,711,869 | 1/1973 | Shea, Jr. . |
| 3,931,648 | 1/1976 | Shea, Jr. . |
| 4,010,820 | 3/1977 | Johnson .................... 181/130 |
| 4,052,754 | 10/1977 | Homsy . |
| 4,130,905 | 12/1978 | Mercandino ................ 623/10 |
| 4,215,438 | 8/1980 | Pappas . |
| 4,252,110 | 2/1981 | Behney . |
| 4,418,787 | 12/1983 | Eggert et al. ............... 181/130 |
| 4,439,154 | 3/1984 | Mayclin ..................... 433/229 |
| 4,510,627 | 4/1985 | Treace et al. . |
| 4,601,723 | 7/1986 | McGrew . |
| 4,624,672 | 11/1986 | Lankauskas . |
| 4,728,327 | 3/1988 | Gersdorff . |
| 4,740,209 | 4/1988 | Gersdorff . |
| 4,871,364 | 10/1989 | Bays et al. . |
| 4,957,507 | 9/1990 | Lenkauskas . |
| 5,306,299 | 4/1994 | Applebaum .................. 623/10 |

*Primary Examiner*—David Isabella
*Assistant Examiner*—Laura Fossum
*Attorney, Agent, or Firm*—Ellsworth R. Roston; Charles H. Schwartz

[57] ABSTRACT

Apparatus for, and a method of, facilitating the hearing of audio information by an individual are provided for the inner ear of the individual. The apparatus includes a prosthesis having a head portion and a body portion. The head portion may be provided with a flattened configuration shaped to confirm to a particular one of the malleus and the incus. The body portion of the prosthesis extends transversely from the head portion into the fluid in the inner ear. The prosthesis may be made from a suitable material such as a metal or a plastic having properties of transmitting sound from the middle ear to the inner ear. A heat shrinkable sleeve envelopes the head portion of the prosthesis and the particular one of the malleus and the incus. The sleeve may be shrunk as by heat to provide a pressed fit with the head portion of the prosthesis and the particular one of the malleus and the incus. The heat may be produced as by a laser.

8 Claims, 1 Drawing Sheet

APPARATUS FOR ENHANCING HEARING IN AN EAR

This invention relates to apparatus for, and a method of, facilitating the hearing of audio information by individuals. The invention particularly relates to a prosthesis for providing for the transmission of audio information to the inner ear.

BACKGROUND OF THE INVENTION

The ear has three primary components, the outer ear, the middle ear and the inner ear. Sound is received in the outer ear and is transmitted through the middle ear to the inner ear. The middle ear has three primary parts—the malleus, the incus and the stapes. At times one or more of these parts ossifies and impedes the transmission of sound vibrations through the middle ear to the inner ear. This tends to occur particularly in individuals with advanced age.

Various prostheses have been provided in the prior art to provide for the transmission of sound vibrations through the middle ear when the different parts of the middle ear are not functioning properly. These prosthesis have had certain disadvantages. One disadvantage is that the prostheses are relatively complicated. Another disadvantage is that the prostheses are not always successful. This invention provides a prosthesis which is relatively simple in construction and which provides for an assured transmission of sound to the inner ear.

BRIEF DESCRIPTION OF THE INVENTIONS

In one embodiment of the invention, apparatus for, and a method of, facilitating the hearing of audio information by an individual are provided for the inner ear of the individual. The apparatus includes a prosthesis having a head portion and a body portion. The head portion may be provided with a flattened configuration shaped to confirm to a particular one of the malleus and the incus. The body portion of the prosthesis extends transversely from the head portion into the fluid in the inner ear. The prosthesis may be made from a suitable material such as a metal or a plastic having properties of transmitting sound from the middle ear to the inner ear.

A heat shrinkable sleeve envelopes the head portion of the prosthesis and the particular one of the malleus and the incus. The sleeve may be shrunk as by heat to provide a pressed fit with the head portion of the prosthesis and the particular one of the malleus and the incus. The heat may be produced as by a laser.

DESCRIPTION OF THE PREFERRED EMBODIMENT

Figure 1:
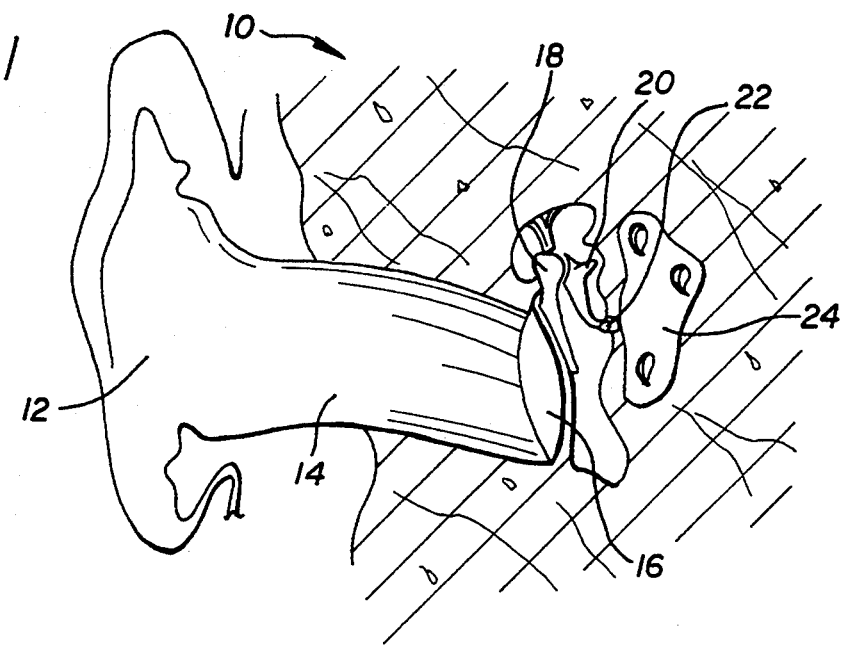
FIG. 1 is a schematic diagram of the different parts of an individual's ear.
Figure 2:
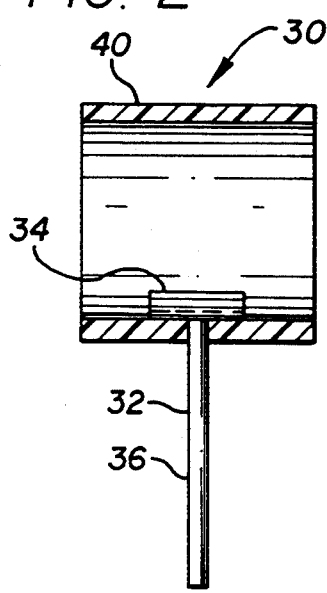
FIG. 2 is a schematic side elevational view, partly in section, of the prosthesis of this invention before heat is applied to the prosthesis.
Figure 4:
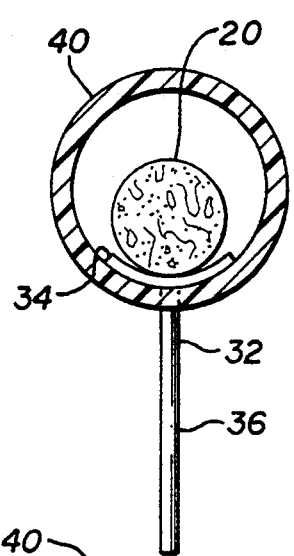
FIG. 4 is a front elevational view, partly in section, of the prosthesis and the incus before heat has been applied to the prosthesis.

FIG. 1 illustrates the different parts of an individual's ear, generally indicated at 10, on a somewhat schematic basis. The ear 10 includes an auricle 12 in an outer ear, an auditory meata 14 in the outer ear and a tympanic membrane 16 in the outer ear. The ear 10 further includes a malleus 18, an incus 20 and a stapes 22 in a middle ear. The malleus 18, the incus 20 and the stapes 22 in the middle ear transmit sound vibrations to a fluid in an inner ear 24.

It may sometimes happen that the malleus 18, the incus 20 and/or the stapes 22 become ossified or otherwise impaired so that sound vibrations cannot be properly transmitted from the outer ear to the fluid in the inner ear 24. At such times the hearing of the individual may become significantly impaired so that the individual does not hear properly.

This invention provides a prosthesis, generally indicated at 30, which can be coupled to the malleus 18 or the incus 20 in the middle ear to provide for the transmission of sound vibrations from the outer ear to the inner ear. The prosthesis 30 includes a member 32 which may be made from a suitable metal or plastic having properties of transmitting sound vibrations. The member 32 includes a head portion 34 shaped to abut the outer surface of the malleus 18 or the incus 20. In FIGS. 2-5, the head portion 34 is shown as abutting the incus 20. The head portion 34 is provided with a flattened configuration and may be curved to conform to the abutting surface of the incus or the malleus. A body portion 36 extends from the head portion 34 in integral relationship with the head portion. The body portion 36 extends in a direction transverse, preferably perpendicular, to the head portion 34. The body portion 36 extends into the fluid in the inner ear to transmit sound vibrations from the outer ear to the inner ear.

A sleeve 40 is disposed in enveloping relationship to the incus 20 (as shown in FIGS. 2-5) or to the malleus and also in enveloping relationship to the head portion 34 of the member 32. Before being subjected to heat, the sleeve 40 may have an annular configuration in section. The sleeve 40 may initially be disposed in a loose relationship to the incus 20 (or to the malleus 22) and to the head portion 34 of the member 32. The sleeve 40 may be made from a suitable material having properties of shrinking when subjected to heat. Such a material is well known in the art.

Figure 5:
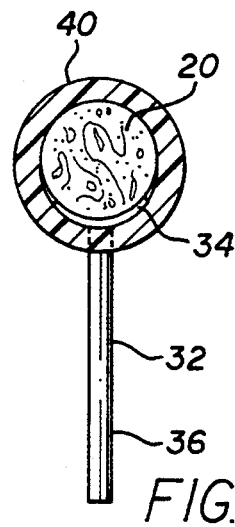
FIG. 5 is a front elevational view, partly in section, of the prosthesis and the incus after heat has been applied to the prosthesis.
Figure 3:
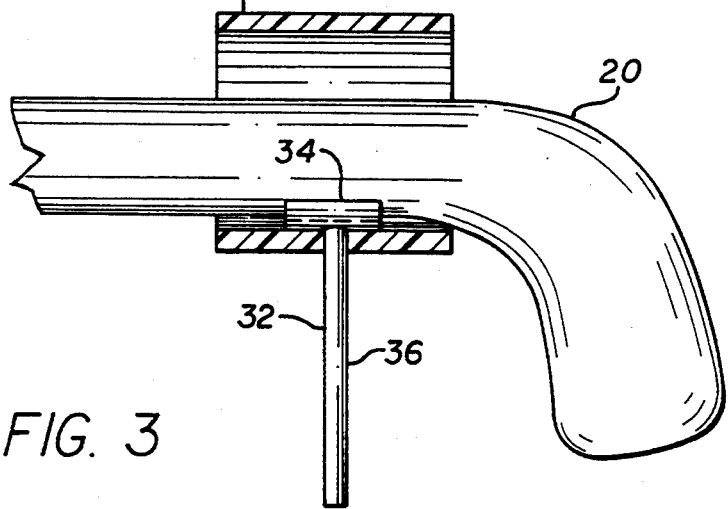
FIG. 3 is a side elevational view, partly in section, of the prosthesis on an incus before heat is applied to the prosthesis.

When heat is applied to the sleeve 40 such as by a laser, the sleeve 40 shrinks to a size where it provides a pressed fit with the incus 20 (as shown in FIG. 5) or with the malleus 22 and with the head portion 34 of the member 32. This causes the member 32 to be retained in a fixed relationship with the incus 20 (as shown in FIG. 5) or with the malleus 22. This is the primary function of the sleeve 40.

The prosthesis 30 described above and shown in the drawings has certain important advantages over the prior art. It provides an effective method of transmitting sound vibrations from the outer ear through a path including the incus 20 (or the malleus), the head portion 34 of the member 32 and the body portion 36 to the fluid in the inner ear. Furthermore, by including the sleeve 40, a simple and efficient way of coupling the prosthesis 30 to the malleus 18 or the incus 20 is provided.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

We claim:

1. An apparatus for facilitating hearing in a middle ear having a malleus and an incus comprising:

a prosthesis having a head portion and body portion, said body portion configured to be coupled to one of the malleus and the incus and fixed thereto by a heat shrinkable tube, said heat shrinkable tube envelopes the head portion and the adjacent portion of one of the malleus and the incus whereby upon application of heat to the tube, the tube shrinks to provide a pressed fit with the head portion and one of the malleus and the incus, thereby fixing the head portion to said adjacent portion of one of the malleus and the incus, and the body portion extends into fluid in an inner ear.

2. An apparatus as set forth in claim 1 wherein the prosthesis is formed from material having properties of vibrating in the normal human audio frequency range, said material selected from the group consisting of plastic and metal.

3. An apparatus as set forth in claim 1 wherein the head portion is flat and shaped to be attached to one of the malleus and the incus and wherein the body portion extends transversely from said head portion to the fluid in the inner ear.

4. An apparatus as set forth in claim 3 wherein the heat shrinkable tube has a hollow annular configuration before the application of heat.

5. An apparatus for facilitating hearing in a middle ear having a malleus and an incus and having fluid in an inner ear comprising:

a prosthesis having a first portion and a second portion, said first portion configured to be coupled to one of the malleus and the incus, said second portion extends transversely from said first portion into the fluid of the inner ear, and means for enveloping the prosthesis and one of the malleus and the incus through application of heat to provide a pressed fit between the prosthesis and one of the malleus and the incus.

6. An apparatus as set forth in claim 5 wherein the prosthesis is made from a material having properties of vibrating in the normal human audio frequency range, the prosthesis extending into the fluid in the inner ear for communicating audio information thereto.

7. An apparatus as set forth in claim 5 wherein the malleus and the incus have a curved shape and the first portion of the prosthesis is curved to conform to the curved shape of one of the malleus and the incus, and the prosthesis is made from a material, said material selected from the group consisting of plastic and metal.

8. An apparatus as set forth in claim 5 wherein the malleus and the incus have outer edges and the first portion of the prosthesis is defined as a head portion, and the enveloping means has a hollow annular cross section before the application of heft, and an inner surface of the enveloping means is configured to be coupled to the head portion of the prosthesis and the outer surface of one of the malleus and the incus to provide a pressed fit between the head portion of the prosthesis and one of the malleus and the incus.

* * * * *